(12) United States Patent
Mavity et al.

(10) Patent No.: US 6,248,057 B1
(45) Date of Patent: Jun. 19, 2001

(54) ABSORBABLE BRACHYTHERAPY AND CHEMOTHERAPY DELIVERY DEVICES AND METHODS

(75) Inventors: William G. Mavity, Los Altos; Robert A. Stern, Mountain View, both of CA (US); Shigemasa Osaki, Sandy, UT (US); Paul O. Zamora, Gaithersburg, MD (US)

(73) Assignee: Innerdyne, Inc., Sunnyvale, CA (US)

( * ) Notice: Subject to any disclaimer, the term of this patent is extended or adjusted under 35 U.S.C. 154(b) by 0 days.

(21) Appl. No.: 09/361,553

(22) Filed: Jul. 27, 1999

Related U.S. Application Data

(60) Provisional application No. 60/094,412, filed on Jul. 28, 1998.

(51) Int. Cl.[7] .................................................. A61N 5/00
(52) U.S. Cl. ...................................................... 600/3
(58) Field of Search .............................................. 600/1–8

(56) References Cited

U.S. PATENT DOCUMENTS

| | | |
|---|---|---|
| 3,976,071 | 8/1976 | Sadek . |
| 4,479,930 | 10/1984 | Hnatowich . |
| 4,668,503 | 5/1987 | Hnatowich . |
| 4,732,864 | 3/1988 | Tolman . |
| 4,832,686 | 5/1989 | Anderson . |
| 4,883,666 | 11/1989 | Sabel et al. . |
| 4,897,268 | 1/1990 | Tice et al. . |
| 5,078,985 | 1/1992 | Rhodes . |
| 5,102,990 | 4/1992 | Rhodes . |
| 5,194,581 | 3/1993 | Leong . |
| 5,225,180 | 7/1993 | Dean et al. . |
| 5,256,765 | 10/1993 | Leong . |
| 5,277,893 | 1/1994 | Rhodes . |
| 5,338,770 | 8/1994 | Winters et al. . |
| 5,371,184 | 12/1994 | Rajagopalan et al. . |
| 5,376,356 | 12/1994 | Morgan, Jr. . |
| 5,382,654 | 1/1995 | Lyle et al. . |
| 5,443,953 | 8/1995 | Hansen et al. . |
| 5,463,010 | 10/1995 | Hu et al. . |
| 5,464,934 | 11/1995 | Dunn et al. . |
| 5,484,584 | 1/1996 | Wallace et al. . |
| 5,543,158 | 8/1996 | Gref et al. . |
| 5,656,297 | 8/1997 | Bernstein et al. . |
| 5,873,811 | * 2/1999 | Wang et al. ................... 600/3 |
| 5,876,452 | 3/1999 | Athanasiou et al. . |
| 5,942,209 | * 8/1999 | Leavitt et al. ................. 600/3 |
| 5,980,551 | 11/1999 | Summers et al. . |

FOREIGN PATENT DOCUMENTS

| | | |
|---|---|---|
| WO 91/06286 | 5/1991 | (WO) . |
| WO 97/46276 | 12/1997 | (WO) . |
| WO 99/21615 | 5/1999 | (WO) . |

OTHER PUBLICATIONS

Ewend et al., "Local delivery of chemotherapy and concurrent external beam radiotherapy prolongs survival in metastatic brain tumor models" Cancer Res. (1996) 56(22):5217–5223.

Jampel et al., "In vitro release of hydrophobic drugs from polyanhydride disks" Ophthalmic Surg. (1991) 22:676–680.

* cited by examiner

Primary Examiner—John P. Lacyk
(74) Attorney, Agent, or Firm—Townsend and Townsend and Crew LLP

(57) ABSTRACT

Combination radiation delivery and chemotherapy devices comprise bioabsorbable structures with radionuclides and chemotherapeutic agents immobilized on said structures. The bioabsorbable structures have a predefined persistence period which is usually substantially greater than the half-life of the radionuclides, thus assuring that the radionuclides remain localized and sequestered at a desired target site while significant radioactivity remains. The radiation delivery and chemotherapy devices are suitable for a wide variety of medical purposes, being particularly suitable for the treatment of solid tumors by injection or open surgical introduction of the devices at a target site. Kits comprising the devices together with instructions for use are also provided.

30 Claims, 5 Drawing Sheets

ABSORBABLE BRACHYTHERAPY AND CHEMOTHERAPY DELIVERY DEVICES AND METHODS

CROSS-REFERENCES TO RELATED APPLICATIONS

This application claims the benefit of the filing of U.S. Provisional Patent Application Ser. No. 60/094,412, entitled "Absorbable Brachytherapy Delivery Devices and Methods for Their Use and Preparation", filed on Jul. 28, 1998, and the specification thereof is incorporated herein by reference.

BACKGROUND OF THE INVENTION

1. Field of the Invention

The present invention relates generally to methods and systems for preparing and using radiation delivery devices and combination radiation and drug delivery devices, such as beads, seeds, particles, rods, gels, and the like. In particular, the present invention relates to methods and systems for preparing and using absorbable radiation delivery devices and combination radiation and drug delivery devices having core elements which will be resorbed in tissue over time.

2. Description of the Background Art

A number of techniques have been proposed to treat tumor growth. Brachytherapy relies on implanting a radiation source to provide localized treatment, as contrasted, for example, with treating a site from a distance by external beam radiation. In prostate brachytherapy, radiation delivered by small "seeds" placed very close to the area being treated are used. Such placement minimizes the chance of affecting nearby tissue, while still delivering adequate radiation to destroy diseased cells.

Ultrasound-guided prostate brachytherapy, also called "interstitial brachytherapy" or simply a "seed implant," is exemplary of minimally invasive brachytherapy techniques. It does not require a hospital stay and typically has no long term side effects. Initially, an ultrasound "volume study" is performed to measure the prostate gland and plan the treatment. A few weeks later, radioactive seeds are inserted using a needle under ultrasound guidance directly into the prostate. The procedure takes about an hour and, after a short recovery period, the patient can usually go home.

While successful in many patients, brachytherapy relies on deposition of metallic seeds that remain in place after treatment. Should the initial treatment be less than fully effective, the continuing presence of the seeds can preclude or restrict a clinician's ability to subsequently image and/or re-treat a tumor.

The preparation of conventional brachytherapy devices is problematic in a number of respects. In particular, the devices are usually fabricated from metal alloys that are subsequently irradiated or plated to become radioactive. The devices so prepared have a limited shelf life. For devices fabricated at a central facility, distribution and inventory maintenance become significant problems. Further, devices fabricated from metal allows are not absorbable. That is, once the device has been fabricated, e.g. by irradiation or plating, its useful life is limited and its metallic core will not degrade. The permanence of the device core is a particular problem in subsequent disease monitoring and treatment. A metallic core that remains at the treatment site can both interfere with radiographic and other imaging of the region (thus making disease monitoring difficult) and prevent certain follow-up therapies.

Biodegradable radioactive implant materials have been made for diagnostic and imaging purposes. For example, a radioisotope may be bound to a biodegradable polymeric matrix where the purpose is usually to provide for controlled release of the radioactive material over time. Such biodegradable radioactive materials are generally not useful for brachytherapy since they release the radioactive material rather than localize it at the desired treatment site.

Radiopharmaceuticals composed of antibodies, peptides, and other localizing substances have been made and injected directly into tumors for radiotherapeutic purposes. During such direct injections a portion of the radiolabeled antibodies, peptides, and the like bind to the tumor. However, a substantial amount of these radiopharmaceuticals are washed out of the tumor by normal clearance mechanisms. The result of this washout is a decreased dose to the tumor and an increased dose to normal organs such as bone marrow, the liver, and kidneys. A number of radio-colloids have been prepared from Re-186, Re-188, Y-90, P-32, Ho-166, Sm-153, and the like, and have been used to treat tumors of cavities such as metastatic pleural effusion, malignant pericardial effusion, peritoneal metastasis cavity and the like. These colloids are delivered by use of an in-dwelling catheter and are designed to provide a thin film of radioactive colloid throughout the cavity. Thus, radiocolloids are useful for treating tumors, tumor metastasis, and diseases of cavities, and irradiate both tumor cells and normal cells lining the cavity. Such colloids have not been used in concert with biodegradable matrices. Some of the colloids, including Re-188 sulfur colloid have been used-to treat liver tumors by injecting them into the vasculature of the liver. This approach, however, can result in considerable shunting of the radioactive materials to the normal lung.

The use of biodegradable or bioerodible materials to provide sustained or controlled release of chemotherapeutic or other drugs, including bioactive drugs, has been known for a number of years. Biodegradable implants for the controlled release of hormones, such as contraceptive hormones, were developed over twenty years ago, and have been used as birth control devices. Biodegradable or bioerodible materials employed for controlled release of drugs include polyanhydrides, polyglycolic acid, polylactic/polyglycolic acid copolymers, polyhydroxybutyrate-valerate and other aliphatic polyesters, among a wide variety of polymeric substrates employed for this purpose. Many of these materials have been characterized by inconsistent drug release kinetics.

For many applications, such as biodegradable implants for controlled release of contraceptive implants, the site of implantation is unrelated to the drug target, and implantation is simply employed as a mechanism for sustained delivery. In some applications, biodegradable polymer implants have been used to directly deliver chemotherapeutic agents to a desired treatment side. For example, polymer implants which release the cancer chemotherapeutic dug carmustine have been used as implants in the surgical cavity created when a brain tumor is removed. As the wafer erodes, it releases the cancer chemotherapeutic drug directly to the tumor site in high concentrations over an extended period of time. (Jampel H D, Koya P, Leong K, Quigley H A. In vitro release of hydrophobic drugs from polyanhydride disks. Ophthalmic Surg 1991; 22:676–680.)

The synergistic effect of combined radiation and chemotherapy has long been appreciated, and is a standard modality of cancer therapy. Prior art methods have frequently employed systemic chemotherapy, where chemotherapy drugs are administered intravenously, orally or by other systemic means, and external radiotherapy is employed, such as external beam radiation. In one instance, biodegradable polymer implants for the treatment of cancer, containing the cancer chemotherapeutic drug carmustine, have been used with concurrent external beam radiation, and found to increase survival in patients with metastatic brain tumors. (Ewend M G, Williams J A, Tabassi K, et al. Local delivery of chemotherapy and concurrent external beam radiotherapy prolongs survival in metastatic brain tumor models. Cancer Res 1996; 56(22):5217–5223) Conventional systemically administered chemotherapeutic agents have also been used in conjunction with implanted brachytherapy devices.

For these reasons, it would be desirable to provide improved methods and devices for the delivery of radioactivity and also chemotherapeutic, bioactive or other drugs to patients for therapeutic purposes. In particular, it would be desirable to provide improved delivery devices which deliver both local radiation and local chemotherapeutic or bioactive drugs, and are degradable after implantation so that they largely or completely disappear from the treatment region over time. The structure or core of such devices, however, should have sufficient permanence or persistence so that the bound radioisotope or other radioactive source material will remain localized at the site of implantation at all times while the emitted radiation remains significant, i.e., above some defined threshold level. It would be further desirable to provide fabrication methods and techniques which permit the construction of delivery devices having a variety of forms, including both relatively large devices, such as seeds, pellets, and other delivery devices of the type commonly used in brachytherapy of tumors and other proliferative diseases, as well as beads, particles, microparticles, and other small forms which can be utilized in other types of treatment. It would be further desirable to provide devices wherein the chemotherapeutic or bioactive drug release rate can be determined prior to use of the device in a patient, so that the drug release rate can be correlated to the radiotherapy rates.

The preparation of biodegradable radioactive materials is described in U.S. Pat. Nos. 5,256,765 and 5,194,581 and PCT application WO 91/06286. Other biodegradable implantable materials, some of which have been used in drug delivery systems, are described in U.S. Pat. Nos. 5,656,297; 5,543,158; 5,484,584; 4,897,268; 4,883,666; 4,832,686; and 3,976,071. U.S. Pat. No. 5,876,452 describes biodegradable polymeric material, such as polyanhydries and aliphatic polyesters, providing substantially continuous release of bioactive drugs, including bi-phasic release of bioactive drugs. U.S. Pat. No. 5,338,770 describes methods and materials for coating biomedical devices and implants with poly(ethylene oxide) chains suitable for covalent attachment of bioactive molecules intended to counteract blood-material incompatibility. U.S. Pat. No. 5,463,010 describes membranes, including polymerized aliphatic hydrocyclosiloxane monomers, for use in coating biomedical devices and implants, and suitable for use as a substrate for covalent attachment of other molecules. A variety of U.S. patents describe various methods for labeling of substrates, typically peptides, proteins and the like, with radioactive metal ions, such as use of DTPA chelates in U.S. Pat. Nos. 4,479,930 and 4,668,503; U.S. Pat. No. 5,371,184, in which a chelate ligand is disclosed for labeling hirudin receptor-specific peptides; U.S. Pat. No. 4,732,864, in which the use of metallothionein or metallothionein fragments conjugated to biologically active molecules is disclosed; U.S. Pat. No. 5,225,180, in which technetium-99 m labeling of peptides containing at least two cysteine residues capable of forming a disulfide bond through reduction of the disulfide is disclosed; U.S. Pat. No. 5,443,953, in which a variety of conjugates for radioisotopes are disclosed; U.S. Pat. No. 5,376,356, in which a variety of methods of radiolabling and conjugates are disclosed; U.S. Pat. No. 5,382,654, in which a variety of bifunctional chelates are disclosed; and U.S. Pat. No. 5,464,934, in which a method of metal chelation, using amino acid sequences that are capable of forming metal complexes, is disclosed. U.S. Pat. Nos. 5,277,893; 5,102,990; and 5,078,985 each describe proteins containing one or more disulfide bonds which are radiolabeled with radionuclides, including technetium and rhenium for use in diagnosis and treatment. U.S. patent application Ser. No. 09/098,072; filed Jun. 16, 1998, describes methods useful in the present invention for coating polymeric and other materials. The full disclosures of each of these patents and pending application are incorporated herein by reference.

SUMMARY OF THE INVENTION

According to the present invention, devices are provided comprising both a radiation delivery component and a drug delivery component immobilized on a bioabsorbable structure. The bioabsorbable structure has a predefined persistence period, i.e., it will remain sufficiently intact after implantation at a target site in patient tissue so that it can localize or sequester the radionuclide at the target site for a minimum threshold time, and further release or disperse the drug, which may be a chemotherapeutic agent, over a complimentary time. The minimum threshold time will usually depend at least in part on the half-life of the radionuclide. In particular, the predetermined persistence period of the bioabsorbable structure will usually be substantially longer than the half-life of the radionuclide, usually being at least two times longer, preferably being at least four times longer, and often being at least ten times longer. In this way, the radionuclide is not released from the bioabsorbable structure until after the persistence period has passed, so that the maximum effect of the radiation is limited to the target, and potential systemic or clearance organ dosage to the patient is below a known or predicted level of safety. In the exemplary devices, the predetermined persistence period of the bioabsorbable structure will usually be in the range from 2 days to 90 days, preferably being in the range from 4 days to 45 days. The lower level of the range will, of course, depend largely on the length of the half-life of the radionuclide since a sufficient time must be provided to permit the radioactivity of the radionuclide to diminish to a safe level. The upper end of the persistence period, in contrast, will preferably be sufficiently short so that the implant has substantially diminished and disappeared from the target site within a period which permits observation and/or further treatment of the disease at the target tissue without interference from the prior implant. Exemplary half-lives for the radionuclides that may be used in the present invention are set forth in the detailed description below.

The drug delivery component of the device includes any drug suitable for treatment of the disease condition for which the device is employed. For cancer and similar neoplastic diseases, this includes any known chemotherapeutic agent, including but not limited to bleomycin, busulfan, carboplatin, carmustine, cisplatin, cladbrbine, dactinomycin, daunorubicin, doxorubicin, estramustine, interferon, levamisole, methotrexate, mitomycin, paclitaxel, pentostatin, plicamycin, tamoxifen, vinblastine, vindesine and the like. This also includes radiosensitizers including 5-halo-uracils, anti-angiogenesis compounds including thalidomide and tranilast, natural or synthetic peptide hormones including octreotide, and compounds that induce apoptosis including butyrate.

The drug delivery component has a predefined release rate, which may be a continuous, bi-phasic or an otherwise modulated release rate. The drug is locally released at the site of the device, and is cleared from the patient by normal clearance and excretory functions. Depending on the disease, choice of radionuclide and choice of drug, the release rate of the drug may be predetermined so that the drug is released within the first two half-lives of the radionuclide, to provide an optimal high-level combination dose of radiation and drug to the site. Alternatively, the drug may be released over the period of predetermined persistence period of the bioabsorbable structure, such as by imbedding or combining the drug within the matrix of the bioabsorbable structure, to provide continued drug delivery to the site even after the radionuclide has substantially decayed.

It is also possible and contemplated that the present invention includes a radiation delivery device comprising a bioabsorbable structure and a radionuclide immobilized on the structure, without the addition or use of a drug or chemotherapeutic agent. Such a radiation delivery device may, but need not, be used in conjunction with drug therapy, including systemic chemotherapy, and other modes of treatment of the disease condition for which the radiation delivery device is employed.

For both devices comprising a radiation delivery component and a drug delivery component for radiation delivery devices, the bioabsorbable structure can be composed of a wide variety of biocompatible materials that are known to degrade with predictable kinetics and over predictable time periods when implanted in patient tissue. The materials will usually be natural or synthetic organic polymers which are prepared to have known and predictable degradation characteristics. While the materials of the biodegradable structures may, in some cases, be the same as those employed in controlled radiation and drug delivery (i.e., where the intent is to release the radioactive material or drug at a controlled rate over time), the present invention relies on selecting the bioabsorbable material to have a sufficient persistence or permanence so that the structure will remain sufficiently intact for a time which allows the radioactivity of the radionuclide or other radioactive material to diminish to a safe level so that it will have no or a negligible adverse effect when released from the bioabsorbable structure.

The biodegradable structures of the devices of the present invention may comprise implantable macrostructures which have continuous core structures with a minimum width or dimension of at least 0.5 mm, usually at least 1 mm. Such devices may be formed to have dimensions and geometries which are similar to known implantable radioactive seeds, pellets, and the like which are presently used in brachytherapy of tumors and other proliferative diseases. Alternatively, the devices of the present invention may be comprised of much smaller implantable microstructures, i.e., particles, beads, or the like, having average widths below 1 mm, usually below 0.5 mm. For either the macrostructures or the microstructures, the material from which they are composed may be swellable or non-swellable when initially implanted at the target site. In all cases, however, the material will be able to remain substantially intact for the predetermined persistence period selected to be compatible with the radionuclide.

The present invention further provides methods for the localized delivery of radioactivity to target sites in tissue, optionally with concurrent sustained release of drugs, including chemotherapeutic agents, at the target site. Particularly, the methods comprise implanting a device of the type described above at said target site. The method of implantation can comprise injecting the device where said device is in the form of an injectable matrix, e.g., the macrostructure or the microstructures, where the microstructures will typically be suspended in a suitable injection medium. Alternatively, the device can be implanted by surgically exposing the target site and placing the device at the surgically exposed site. Such surgical implantation will usually be used with larger devices.

The methods of treatment are particularly suitable for use in treatment of prostate cancer and other conditions, more particularly using methods for ultrasound-guided prostate brachytherapy as described in the background section above. In such cases, the methods can be performed generally as done previously, with the primary difference being that the biodegradable devices of the present invention, which deliver localized radiotherapy and optionally localized chemotherapy, are delivered rather than the prior brachytherapy devices. The devices and methods of the present invention are also useful for the treatment of other cancers, particularly solid tissue cancers, such as breast cancer, liver cancer, kidney cancer, prostate cancer, brain cancer, and the like.

The methods and devices of the present application may also used for the concurrent or successive delivery of genes, peptides, and other active agents which may be incorporated into the bioabsorbable structure. For instance, a peptide may be incorporated uniformly throughout the bioabsorbable structure so that the peptide is released continuously as the structure degrades. Alternatively, a drug to enhance the effect of local delivery of radiation may be coated onto or immobilized within an outer surface or layer of the structure so that the drug is delivered very early while the radiation remains at a high level. Such structure may be particularly useful for gene delivery and therapy where it is presently believed that radiation may enhance cellular transfection.

The present invention still further provides methods for preparing radiation delivery devices and combination devices comprising both radiation and drug delivery devices. Such methods comprise providing a bioabsorbable structure having a predefined persistence period, as discussed above. A radioactive material is then bonded to a surface on the bioabsorbable structure, where the persistence period of the bioabsorbable structure is substantially longer than that of a half-life of the radionuclide. The surface to which the radionuclide is bonded may be an exposed surface on the device, or optionally may be a surface which is subsequently covered or coated with a biodegradable protective layer which prevents or delays premature loss or release of the radionuclide from the device. In particular, the protective layer or material will be formed from a biodegradable substance having known degradation characteristics so that the protective layer will remain in place for a known period, typically the entire persistence period which is desired for the delivery device. It will be appreciated that the resulting devices may thus be constructed to degrade uniformly over time, where the radionuclide or other radioactive material is sufficiently coated, buried or otherwise protected within the structure so that material will cover or coat the radioactive material for a time which is equal to at least the persistence period or a portion thereof during which it is desired to prevent the release of the radioactive material.

Suitable radioactive materials have a half-life of 10 days or less, usually being less than 5 days, and often being in the range from 5 minutes to 3 days, more usually from 1 hour to 2 days. The materials will be capable of being attached directly or indirectly to the biodegradable structure and will emit either singly or in some combination gamma rays, x-rays, positrons, beta particles, alpha particles, or Auger electrons. Any of a wide variety of radioactive materials employed for brachytherapy may be employed in this invention, including but not limited to radioisotopes such as I-125, I-131, Y-90, Re-186, Re-188, Pd-103, Ir-192, P-32 and the like, but may also consist of any other radioisotope with an acceptable half-life, toxicity, and energy level. Thus, the radioisotope my include a radioactive metal ion, such as radioisotopes of rhenium, but may include radioactive metal ions found in the group consisting of elements 26–30 (Fe, Co, Ni, Cu, Zn), 33–34 (As, Se), 42–50 (Mo, Tc, Ru, Rh, Pd, Ag, Cd, In, Sn) and 75–85 (Re, Os, Ir, Pt, Au, Hg, Tl, Pb, Bi, Po, At), and particularly the radionuclides Cu-162, Cu-64, Cu-67, Ru-97, Rh-105, Pd-109, Sm-153, Ho-166, Re-186, Re-188, Au-198, Au-199, Pb-203, Pb-211, and Bi-212.

Suitable isotopes for use in this invention include, but are not limited to, the following:

| ISOTOPE | HALF-LIFE | PRIMARY DECAY MODE |
|---------|-----------|--------------------|
| Cu-62   | 9.8 m     | β−, β+             |
| Cu-64   | 12.9 h    | β−                 |
| Cu-67   | 2.6 d     | β−                 |
| Ru-97   | 2.9 d     | EC                 |
| Y-90    | 2.7 d     | β−                 |
| Rh-105  | 1.5 d     | β−                 |
| Pd-109  | 13.5 h    | β−                 |
| Re-186  | 3.8 d     | β−                 |
| Re-188  | 16.7 h    | β−                 |
| Au-199  | 3.2 d     | β−                 |
| Pb-203  | 2.2 d     | EC                 |
| Pb-211  | 36.1 m    | β−                 |
| Bi-212  | 1 h       | β−, α              |

The radioactive material may comprise a bonding component suitable for covalent or non-covalent attachment to the substrate material, preferably being suitable for covalent attachment. In an exemplary embodiment, bifunctional chelates are covalently or otherwise bonded to the substrate material, preferably through an amine functional group bonded to the substrate material, which substrate material may include a siloxane coating, including an aliphatic hydrocyclosiloxane polymer coating, and the bifunctional chelate is then radiolabeled. A variety of bifunctional chelates can be employed; most involve metal ion binding to thiolate groups, and may also involve metal ion binding to amide, amine or carboxylate groups. Representative bifunctional chelates include ethylenediamine tetraacetic acid (EDTA), diethylenetetramine-pentaacedic acid (DTPA), chelates of diamide-dimercaptides (N2S2), and variations on the foregoing, such as chelating compounds incorporating N2S3, N2S4 and N3S3 or other combinations of sulfur- and nitrogen-containing groups forming metal binding sites, and metallothionine. It is also possible, and contemplated, that a substrate material will be employed to which metal ions may be directly bonded to the substrate material, in which case the substrate material may include an amine functional group bonded to the surface of the substrate material.

As an alternative to chemical bonding, the radioisotopes can be attached to the surface of the micro or macrostructure by other known techniques, such as electroplating, electroless plating, adsorption, and ion pairing.

The drug or chemotherapy agent, if provided, may be uniformly dispersed through the bioabsorbable structure, or may alternatively be dispersed or incorporated in a graduated manner, such that the amount and rate of release of drug or chemotherapy agent either increases or decreases as the bioabsorbable structure is biodegraded or bioeroded. It is also possible and contemplated that the drug or chemotherapy agent will be dispersed or incorporated in a graduated manner such that the amount of drug or chemotherapy agent released over a given period of time is constant throughout the period of persistence of the bioabsorbable structure. Thus, if the rate of release is related to the total surface area of the bioabsorbable structure, then the rate of release may be varied by increasing the concentration of drug or chemotherapy agent on the inner portions of the bioabsorbable structure, such that the amount released remains constant over a given period of time.

In another aspect of the invention, the drug or chemotherapy agent, if provided, may be attached to the bioabsorbable structure, or to a substrate material, if provided, by any means known in the art. The drug or chemotherapy agent may be attached to a surface of the bioabsorbable structure by means of chemical conjugation, or may be included within a coating or other structure forming a part of the bioabsorbable structure. The drug or chemotherapy agent may be within a composition which is layered on the bioabsorbable structure, the composition itself having a known and predetermined rate of biodegradation or bioerosion. Multiple layers of such composition may be provided, thereby providing for release of the drug or chemotherapeutic agent over a longer period of time. Similarly, the composition layered on the bioabsorbable structure may beneficially retard biodegradation or bioerosion of the bioabsorbable structure, such that the bioabsorbable structure itself does not degrade or erode until the radioactive material has substantially decayed.

The chemotherapeutic agent or drug may also comprise a discrete part of unit of the device. For example, the chemotherapeutic agent or drug may be encapsulated, and the encapsulated chemotherapeutic agent or drug may be dispersed throughout the bioabsorbable structure, may be physically imbedded within the matrix of the bioabsorbable structure, or may form a discrete and specific part of the device, such as dispersed within a groove, cavity, slot, hole or other aspect of the bioabsorbable structure. The chemotherapeutic agent or drug may be encapsulated within a liposome, colloid, aggregate, particle, flocculate or other such structure known to the art for encapsulation of drugs. The encapsulation material itself may have a known and predetermined rate of biodegradation or bioerosion, such that the rate of release and amount released is a function of the rate of biodegradation or bioerosion of the encapsulation material.

In another aspect of the present invention, kits are provided including an absorbable radiation delivery device or a combination absorbable radiation delivery and chemotherapy or drug deliver device, and instructions describing a method for implanting the device in patient tissue for treating a solid tumor or other disease. The device will typically be packaged in a conventional medical device package, such as a box, pouch, tray, tube, or the like. The instructions may be printed on a separate sheet of paper, or may be partly or entirely printed on the device package. The implantable device within the package may be sterilized or unsterile.

DESCRIPTION OF THE SPECIFIC EMBODIMENTS

Devices according to the present invention may take any of a wide variety of conventional forms intended for subcutaneous, percutaneous, or open surgical implantation into patient tissue for the treatment of proliferative or other diseases, most typically for treatment of solid tissue tumors.

Figure 1:
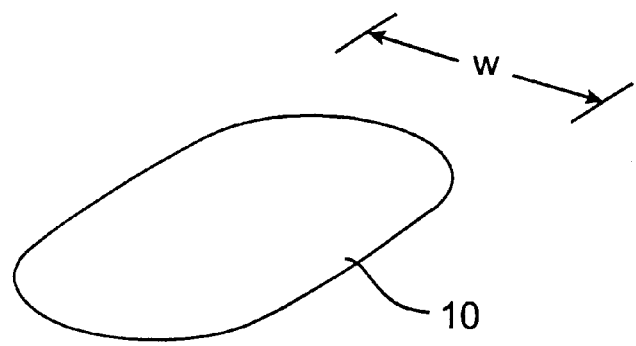
FIG. 1 illustrates a macrostructure radiation delivery device constructed in accordance with the principles of the present invention.

Exemplary devices include macrostructures, microstructures, or a combination of macrostructures and microstructures. The macrostructures may be comprised of natural or synthetic materials which are known to be or can be made to be biodegradable. Macrostructures include devices with geometries which can be represented as spheres, seeds, lozenges, rods, strips, cylinders, or other geometries, including those known to those skilled in the art of brachytherapy, and as illustrated in FIG. 1; or gels, sols, or matrices which can form macrostructures of fixed or malleable geometries. Microstructures include colloids, aggregates, particles, and flocculates which can be used separately or in combination with a macrostructure. When used with a macrostructure, the microstructures can be attached to the outer surface, embedded within a thin protective film overlaying the macrostruture, dispersed within a groove, cavity, slot, hole or other aspect of the macrostructure, or embedded within the matrix of the macrostructure. The macrostructure will be implanted as a unit although a multiplicity of macrostructures can be implanted in any given organ. If a multiplicity of macrostructures are used they would typically be placed at a center-to-center distance related to the energy level of the radioisotope, the treatment zone and the rate of release of the chemotherapeutic agent or drug. Thus, such macrostructures might be placed at a distance of 1 cm center-to-center, or at such other distance as would effect optimal therapeutic effect. If the microstructures as used separately, they would typically be implanted in large numbers, frequently in a mass in a fluid carrier, and may undergo gelation upon interaction with tissue components. It is contemplated that the fluid carrier of the microstructures can undergo gelation or solidification in situ thereby forming a protective biodegradable matrix which forms part of the present invention, i.e., the microparticles will be ultimately imbedded in a hardened matrix which then degrades over time. The particles themselves, of course, will also be ultimately biodegradable so that the entire injected mass will not interfere with subsequent diagnostic imaging of the patient or follow-up therapy.

Illustrative, but not restrictive examples of natural biocompatible, bioabsorbable materials which are contemplated for use in the macrostructures include gels, hydrogels, gel precursors and the like composed of proteins, complex carbohydrates, glycoproteins, glycosaminoglycans, or the like. Natural materials of the extracellular matrix or materials involved in forming cell-to-cell junctions are thought to be particularly attractive as natural bioabsorbable materials. Such biocompatible materials may be composed of materials which gel such as fibrin; elastin; any of the various subtypes of collagen such as collagen type I, collagen type II, collagen type III, collagen type IV and so on; extracts of basement membrane including commercially available materials such as Matrigel™; denatured or polymerized proteins including serum albumin and gelatin; laminin or fragments thereof; fibronectin or vitronectin; glycosaminoglycans and proteoglycans such as hyaluronan, aggregan, chondroitin sulfate, hyaluronic acid, heparin, heparin sulfate; complex carbohydrates such as dextran, dextran derivatives, cyclodextrans, agar, and agarose; as well as complexes or mixtures of any of the foregoing. The gels may also be produced in situ from precursors such as by controlled production of fibrin by the enzymatic degradation of fibrinogen or the gelation of collagen upon neutralization from acidic solutions with warming. Combinations of the various aforementioned materials may also be used. These materials may also be used as binding substrates to bind radioactivity via direct covalent binding, chelation, hydrophobic interaction, ion-pairing and other means known in the art. These materials may further have chemotherapeutic agents or drugs dispersed throughout, or may have such chemotherapeutic agents or drugs bound thereto. In some cases it is contemplated that the rate of degradation of the matrix material can be controlled by overcoating or mixing with synthetic organic polymers.

Illustrative but not restrictive examples of synthetic organic biocompatible, bioabsorbable materials include hydrogels and biodegradable polymeric materials, such as polyanhydrides or aliphatic polyesters. The polymeric materials may be hydrophobic or constructed to be hydrophilic. Polymeric materials include polylactic acid, polyglycolic acid and mixtures thereof, with an average molecular weight between about 10,000 daltons and about 100,000 daltons. It is also contemplated that the synthetic organic material may gel upon introduction into the body. Non-limiting examples of such organic materials are radiolabeled sucralfate or a cyanomethacrylate mixed with a radiolabeled colloid. Sucralfate is a complex of sulfated carbohydrate residues which is complexed to aluminum. This material is normally used for the treatment of ulcers. In aqueous solutions it is a colloid, however, upon exposure to proteins, it binds to the proteins and forms a dense sol which is only slowly absorbed. Cyanomethacrylates would also bind proteins and form macrostructures of the type contemplated in this invention.

Illustrative but not restrictive examples of synthetic organic biocompatible, bioabsorbable materials include polymeric substances synthesized chemically or by other means from amino acids, amino acid mimetics, sugars, sugar mimetics, or variations thereof including blends or mixtures.

The synthetic organic materials may be designed to be dissolved in ethanol such that when injected, the organic materials undergo polymerization trapping the radioactive materials within its matrix while the ethanol diffuses out and acts locally as a denaturant to kill tumor cells. This would provide a two-phase anti-tumor effect which would be an improvement over each one alone.

In one preferred aspect of the invention, the organ to undergo the brachytherapy is surgically debulked and the residual space filled with the radioactive bioabsorbable material which undergoes in situ gelation. Various gelatins, sucalfate, or other bioabsorbable material which undergoes in situ gelation might be employed for such purposes. Radiolabeled sucralfate used in this manner would bind to the proteins in the tissue undergoing a phase transition to a highly hydrated sol. The radioactivity associated with the sucralfate would then irradiate the tumor while the hydrated sol would slowly undergo absorption. The sucralfate or other bioabsorbable material could further comprise a chemotherapeutic agent or drug, which chemotherapeutic agent or drug could optionally be dispersed within a bioabsorbable microstructure dispersed within the sucralfate or other bioabsorbable material. In another aspect of the invention, the organ is "cored" with an array of needles and the cores back-filled with the absorbable radioactive material, optionally further containing a chemotherapeutic agent or drug, which undergoes in situ gelation or solidification. Such a procedure could be used in a non-limiting sense in brachytherapy of the prostate.

It is also contemplated that the microstructures may be supported within the matrix of the macrostructure. Microstructures include colloids, aggregates, liposomes, particles, or flocculates. Non-limiting examples would be a fibrin gel with radioactive colloid suspended within it; a hydrogel with radiolabeled liposomes suspended within it; a polymeric macrostructure with radiolabeled macroaggregated albumin suspended within it; a collagen gel with radiolabeled, activated charcoal within it; or any of the foregoing further including liposomes, particles, flocculants or other microstructures containing or having dispersed therein a drug or chemotherapeutic agent. The methods of producing radioactive colloids such as Re-186 or Re-188 sulfur colloid, Y-90 silicate colloid, P-32-chromic colloid, radiolabeled macroaggregated albumin, and radiolabeled particles are known to those skilled in the art.

In the use of this invention it need not be that the macrostructures nor the microstructures be entirely bioabsorbed. For example if fibrin or collagen is used to provide the macrostructure, such materials are biodegradable yet can persist in the extracellular matrix for substantial lengths of time.

The methods of treatment are particularly suitable for the treatment of solid tumors and metastasis of solid tumors where conventional brachytherapy is currently applied, and in particular cancers of the prostate, lung, breast, and brain as well as head and neck cancers and melanomas. The methods of treatment can be used alone or in combination with other radiation therapies and non-radiation therapies. The methods of treatment are particularly suitable for use in the treatment of prostate cancer with ultra-sound guided placement. The treatments can be planned such that the devices be surgically-placed, injected, or overlayered. For example, the devices can be surgically-placed in recurrent breast cancers which reappear in sites where surgical removal is not a treatment option. The devices can be used following surgical, chemical, or cyro-debulking. The devices may also be constructed such that the device is formed in sheets or plates for the treatment of skin cancers. Such a sheet could be particularly useful in the treatment of AIDS-related Kaposi's sarcoma or melanoma wherein the patient is immune compromised.

Figure 2:
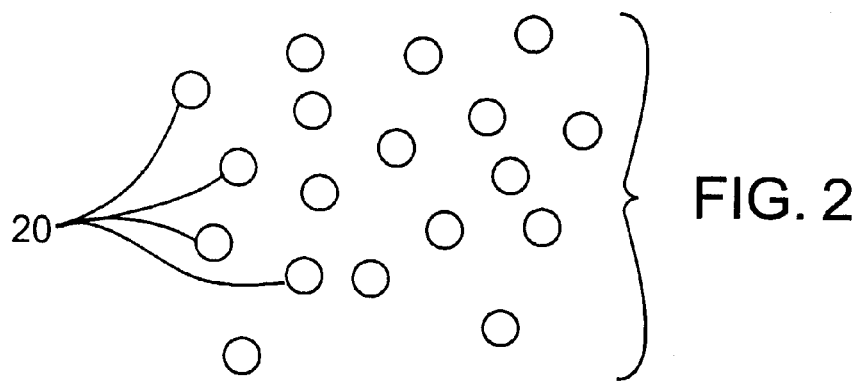
FIG. 2 illustrates a radiation delivery device according to the present invention comprising a plurality of microstructures, such as spherical beads.

Specific macrostructures, such as seed or lozenge 10, are illustrated in FIG. 1, and microstructures, such as particles 20 are illustrated in FIG. 2. The macrostructures will typically be implanted individually or in a relatively small number at a target site in solid tissue, typically being from 1 to 10, more typically from 1 to 5. The microstructures, in contrast, will typically be implanted in much larger numbers, frequently being implanted in mass in a fluid carrier. It is possible that the fluid carrier could itself be curable to form a protective biodegradable matrix which forms part of the present invention, i.e., the microparticles will ultimately be imbedded in the hardened matrix which then degrades over time. The particles themselves, of course, will also be biodegradable so that the entire injected mass will disappear to permit subsequent imaging, diagnosis, and therapy of the patient at the previously treated target site. Macrostructures, such as seed 10, will typically be characterized by minimum widths, e.g., about 0.5 mm, usually about 1.0 mm. The microstructures, in contrast, will typically have average sizes below about 250 $\mu$m, more usually below about 20 $\mu$m.

Figure 3:
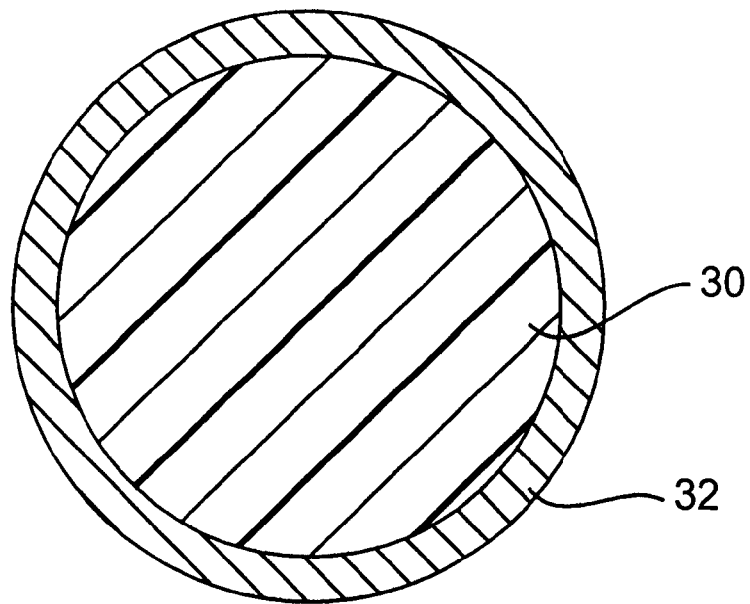
FIG. 3 illustrates a cross-sectional view of a bioabsorbable structure comprising a core structure coated on its exterior surface with a radioactive material.
Figure 4:
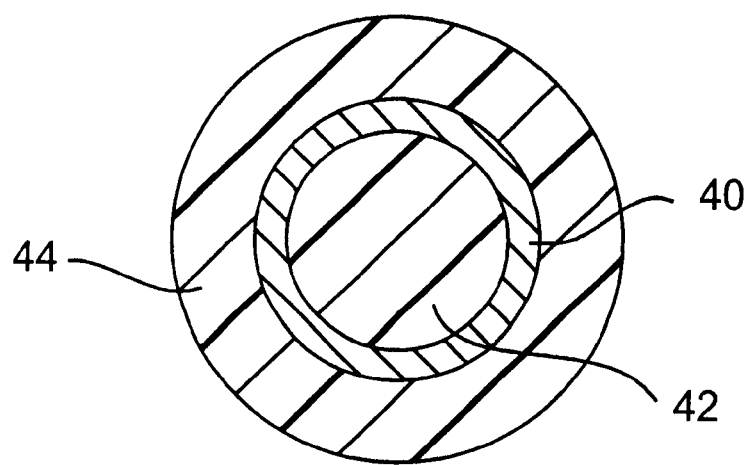
FIG. 4 illustrates a bioabsorbable structure comprising a core particle having a buried radioactive layer.

The device will usually comprise both a bioabsorbable structure having a predefined persistence, as discussed above, and a radionuclide having a known half-life. The radionuclide will be immobilized on or within the bioabsorbable structure, where the persistence period of the structure will assure that the radioactive material remains localized at the target site to which the device has been delivered for a time sufficient to permit the radioactivity to degrade to a safe or negligible level. The radionuclide may be coated over a surface of the bioabsorbable structure, with exemplary coating techniques described in detail below. The coating may occur in a variety of ways. For example, as shown in FIG. 3, a bioabsorbable structure 30 may be coated over its exterior surface with a radioactive material containing a desired radionuclide formed as a layer 32, thereover. The bioabsorbable structure 30 thus defines a structural core which will remain largely intact during the persistence period of the radioactivity so that an acceptable level, preferably none, of the radioactive material in layer 32 is released from the structure. A drug or chemotherapeutic agent may be included within the layer 32, or alternatively within the bioabsorbable structure 30. Alternatively, as illustrated in FIG. 4, a radioactive layer 40 may be formed over an inner core 42 of the bioabsorbable structure, where the radioactive layer is further covered with an outer coating or layer of bioabsorbable material 44. In such cases, the bioabsorbable material may be selected to degrade uniformly over time, where the thickness of the layer 44 defines the persistence period, i.e., that period of time in which the radioactive layer 40 will be protected and not be lost from the structure. The layer 44 may further comprise a chemotherapeutic agent or drug dispersed therein, such that the chemotherapeutic agent or drug is released from the device during the persistence period of the radioactivity.

In other embodiments, the radioactive material may be uniformly or non-uniformly dispersed within a matrix of the material of the bioabsorbable structure. In such instances, it will be necessary that the bioabsorbable structure remain largely intact for a time sufficient to provide the desired persistence period. That is, the nature of the bioabsorbable material will be selected so that the structure will not begin to degrade for some minimum threshold of time during which it is desired to sequester and immobilize the radioactive material. Such bioabsorbable structure may optionally be coated with a material including therein a chemotherapeutic agent or drug, such that the chemotherapeutic agent or drug is released during the period of persistence of the radioactivity.

Once the bioabsorbable structures are formed, the radionuclides or other materials may be immobilized over a surface thereof. A list of suitable radionuclides and their half-lives is set forth above. When the structure is not polymeric in nature, the surface may be covered with a siloxane material which provides a linking moiety for subsequent bonding of suitably modified radionuclides. Suitable substrate materials include the siloxane surface materials described in U.S. Pat. Nos. 5,338,770 and 5,463,010. The siloxane material forms a smooth, continuous thin coating or membrane, and may be produced as described in U.S. Pat. Nos. 5,338,770 and 5,463,010. The siloxane material coats a surface of the bioabsorbable structure, where the surface may be left uncovered or may be subsequently covered or coated with additional layer(s) of bioabsorbable material(s), and a plurality of amine functional groups are bonded to the siloxane surface. The metal ion may be bound directly to one or more of the amine groups. If an isotope of rhenium is employed, such as Re-186 orRe-188, then the rhenium may be reduced to an appropriate redox state, using a stannous reducing agent or other reducing agents known in the art, to facilitate binding to the amine functional groups.

It is also contemplated that a variety of linker technology may be employed, in which a radioactive metal ion is bound to a bifunctional chelate, which directly or through a series of linking agents is in turn bound to the substrate material. The linking agents may be formed from the conjugation compounds containing aldehydes, amines, thiol or sulfhydryl groups, carboxyl groups, alcohols or other reactive group containing nitrogen, oxygen, and carbon. The linking agents may also be sued to generate or attach additional reactive groups containing aldehydes, amines, thiol or sulfhydryl groups, carboxyl groups, alcohols or other reactive group containing nitrogen, oxygen, and carbon.

In one example, the siloxane material as above has bonded to its surface a plurality of amine functional groups. Covalently bonded to the amine functional groups are a plurality of poly (ethylene oxide) chains, such that a single poly (ethylene oxide) chain is bonded to a single amine functional group, all as is generally described in U.S. Pat. No. 5,338,770. A quantity of at least one molecule containing at least one reactive sulfide, or one disulfide bond, and a reactive amine is covalently bonded to the poly (ethylene oxide) chains. In the event that a disulfide bond is employed, such as with a cystine, a reducing agent, such as a stannous reducing agent, may be employed to simultaneously reduce the disulfide bond in the bifunctional chelate, and to reduce the metal ion, such as an isotope of rhenium, to an approximate redox state for forming a stable bond. The metal ion is then reacted with the reactive sulfide, which reactive sulfide is either originally present or formed through reduction of a disulfide bond, and the metal ion is bound to the reactive sulfides and available reactive amines, forming a metal ion complex. Means to attach or complex disulfide bonds, and chelating agents and substrates containing disulfide bonds, are known to those skilled in the art. Disulfide bonds may be introduced into such proteins by chemical methods involving direct conjugation. Chemical means used to introduce disulfide bonds into proteins include use of homofunctional crosslinkers and heterofunctional crosslinkers. Representative chemicals which can be used to introduce disulfide bonds include 4-succinimidyloxycarbonyl-alpha-methyl-alpha-(2-pyridyldithio)-toluene; N-succinimidyl 3-(2-pyridyldithio)propionate; sulfosuccinimidyl 6-[3-(-pyridiyldithiol) propinoamido]hexonate; dithiobis (succinimidylproprionate); 3,3'-dithiobis (sulfosuccinimidylpropionate); and sulfosuccinimidyl 2-(p-azidosalicylamido)ethyl-1,3'dithiopropionate.

It is also possible and contemplated to have bifunctional chelating agents covalently or otherwise bonded to the substrate material, in one embodiment through an amine functional group bonded to the substrate material, which substrate material may include a siloxane coating, including an aliphatic hydrocyclosiloxane polymer coating as described above. Representative bifunctional chelating agents include agents based on aminocarboxylic acids, such as EDTA and cyclic anhydride of DTPA; agents based on triamines, including those disclosed in U.S. Pat. No. 5,101,041; and thiol-containing agents, including the agents disclosed in U.S. Pat. Nos. 5,443,815 and 5,382,654. The bifunctional chelating agent may also be a peptide sequence, composed of natural or unnatural amino acids, covalently or otherwise bonded to the substrate material, including through functional amine groups bonded to the substrate material. Representative peptide sequence bifunctional chelating agents including the amino acid sequences:

-Gly-Gly-Cys-

-Cys-Gly-His-

-Asp-Gly-Cys-

-Glu-Gly-Cys-

-Gly-Asp-Cys-

-Gly-Gly-Cysand modifications of the foregoing, including substitution of Pen for Cys, and the unnatural amino acid sequences as disclosed in U.S. Pat. No. 5,464,934.

It is also possible and contemplated to have substances or chemical groups which are used to attach radioactive iodine or other halogens. In one embodiment, poly-tyrosine is attached through the "N"-terminal amine to the substrate, thereafter it is chemically modified such that radioactive iodine is bonded to the tyrosine. Methods for such introduction of radioactive iodine into tyrosine is known to those skilled in the art and may involve an oxidative process involving chloramine T or the like. The iodine may also be introduced into a large variety of acceptable substrates which generally contain a benzene-like ring or vinyl-group.

In each instance, the bioabsorbable structure, or a portion thereof, may be radiolabeled by means known to the art. In one embodiment, using any of the substrates set forth above to which is bonded a chelating agent, the device is placed in an solution containing the radionuclide, reducing agents as required to reduce the radionuclide and disulfide bonds, if present, including stannous reducing agents, appropriate buffers and the like. Depending on the radionuclide, the solution with the device may be heated to any temperature up to boiling temperature, and may be incubated for any required period. The amount of radioactivity bonded to the implantable device may be controlled by varying the concentration of radioactivity in the solution and by varying the reaction conditions, including pH, temperature and the length of incubation.

The radioactively coated structures, optionally containing chemotherapeutic agents or drugs dispersed therein or coated thereon, may then be introduced to the patient in a conventional manner, depending on the device. In the case of absorbable brachytherapy seeds, the seeds may be surgically implanted or be delivered by means of a needle. The delivery needle may be modified to provide for shielding of the radioactive seeds, and methods for constructing shielded needles are well described in the patent literature.

Figure 5A:
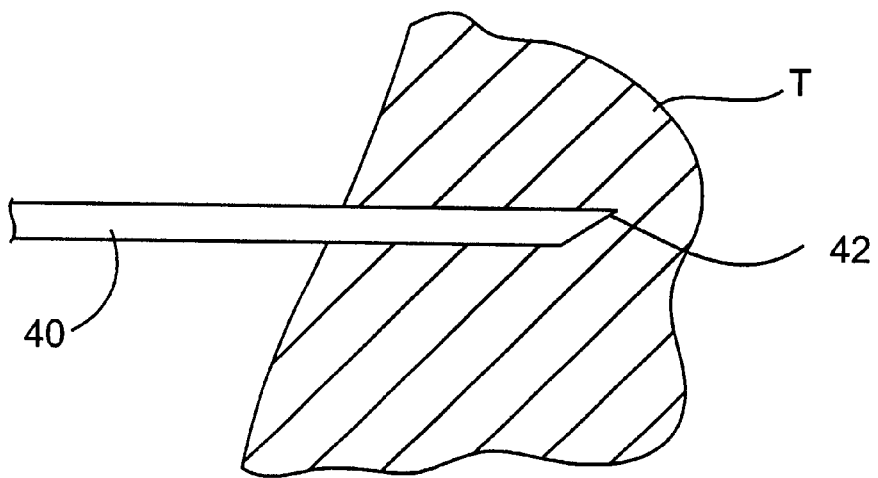
FIGS. 5A–5C illustrate a method according to the present invention for delivering a radioactive delivery device to solid tissue.
Figure 5B:
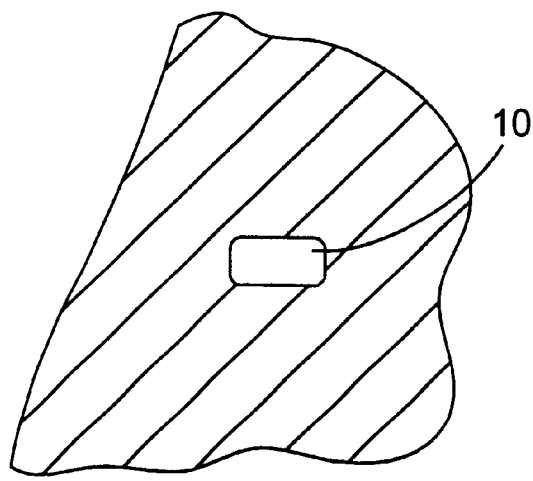
Figure 5C:
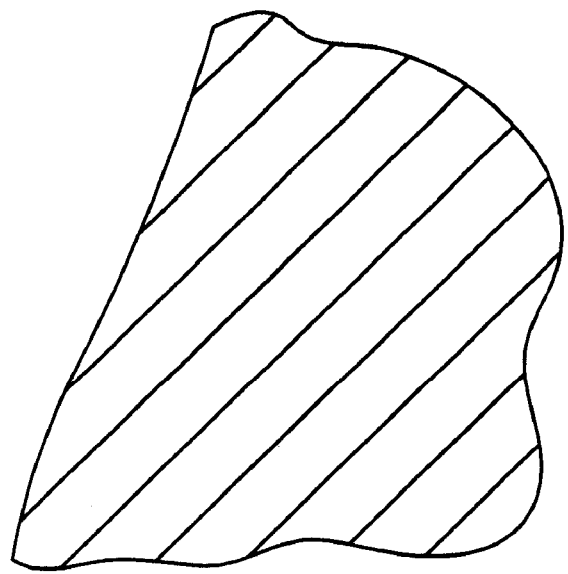

Referring now to FIGS. 5A–5B, the seed 10 illustrated in FIG. 1 may be introduced to a site in solid tissue T using a needle or other introducing cannula 40. The distal tip 42 of the needle 40 is located at a desired target site within the tissue, typically using ultrasonic or fluoroscopic imaging. The seed 10 may be introduced to the target site through the cannula 40, and the cannula withdrawn leaving the seed 10 at the target site, as illustrated in FIG. 5B. Over time, but after the radioactivity of the seed has diminished to a safe level, the bioabsorbable substrate will be absorbed, eventually leaving little or no trace, as illustrated in FIG. 5C. Thus, the treating physician is free to both monitor the target site, typically through radiographic or other imaging, as well as to subsequently treat the target site without interference from any permanent implant, such as the metallic seeds frequently used in prior brachytherapy techniques.

Figure 6:
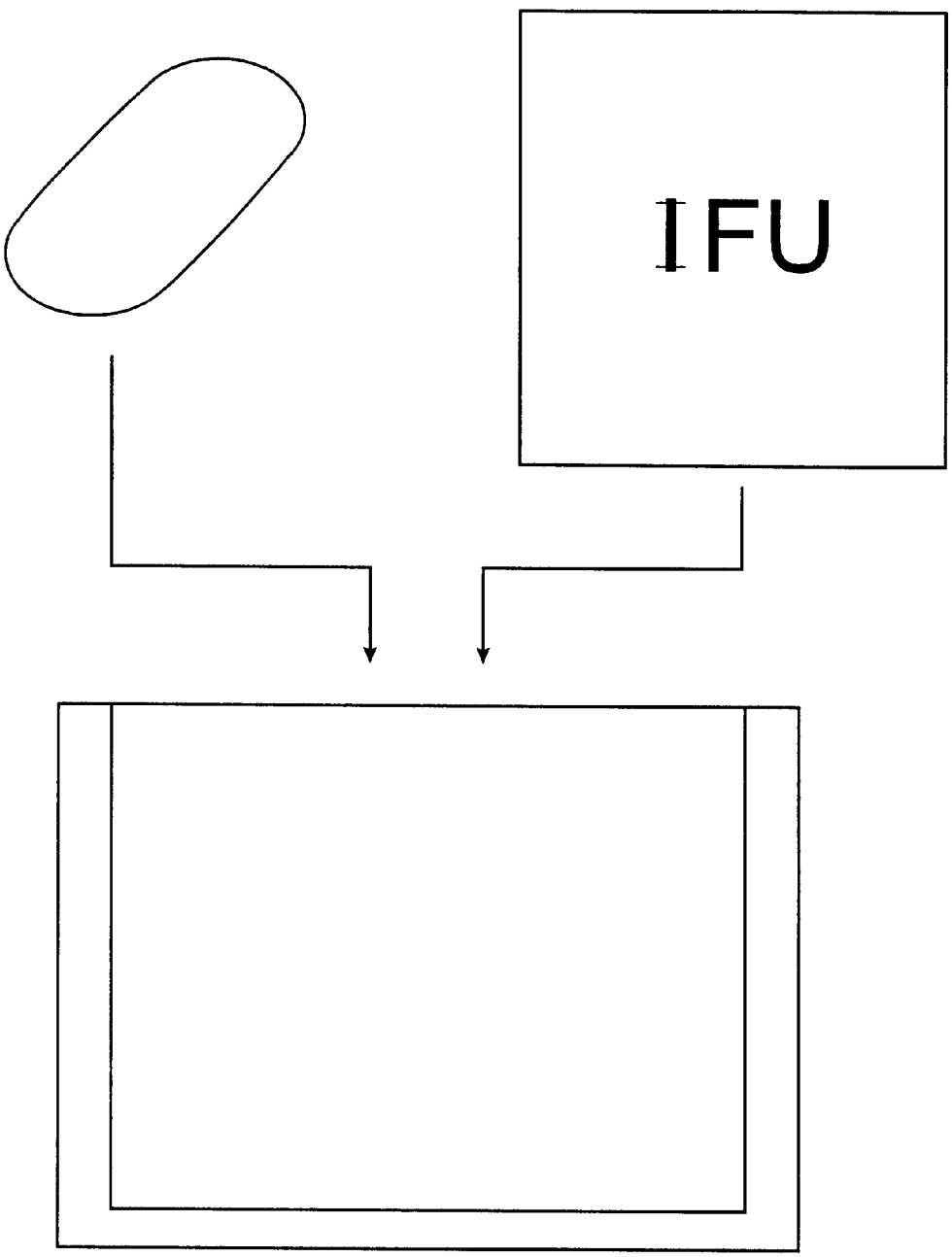
FIG. 6 illustrates a kit according to the present invention.

The implantable absorbable devices of the present invention will typically be provided in kit form, as illustrated in FIG. 6. In particular, FIG. 6 illustrates an implantable seed 10 which has been coated with the substrate material, but which have not yet been coated with the radioactive material. The implantable seed 10 may optionally included dispersed therein or coated thereon a chemotherapeutic agent or drug. The seed 10 will be packaged inside a suitable medical device package, such as pouch 30, and instructions for use IFU will be provided within or on the pouch 30. The instructions for use will describe both coating of the seed 10 with the radioactive material and the subsequent implantation of the seed to a patient target site of interest according to any of the methods of the present invention described above.

The invention is further illustrated by the following non-limiting examples.

EXAMPLE 1

Cast poly-lactide acid-based devices with a microporous structure are obtained as rods. The rods have dimensions of 1.1 mm×15 mm, and are similar to poly-L-lactide tacks in clinical use for fixation of ruptures of the ulnar collateral ligament of the thumb.

The surfaces of the device are exposed to a plasma-state polymerization process with 1,3,5,7-tetramethyl-hydrocyclo-tetrasiloxane (TMCTS) (trademarked Hydrosilox®). The plasma generates a vapor phase plasma zone that consists of an abundance of free radicals, ions and electrons which derive from the TMCTS monomer.

The TMCTS-coated surfaces are then subjected to plasma grafting of N-trimethylsilyl-allylamine (trademarked Grafamine(®). This process attaches hydrolysis-resistant primary amino groups to the surface. Polyethylene glycol (PEG) tethers are then conjugated to the surface amines using a high concentration of poly(oxyethylene)bis-(N-hydroxybenzotriazolyl) carbonate.

Cross-linking techniques are used to synthesize a cross-linked high molecular weight heparin from commercially available heparin (10,000 MW, nominal). This cross-linked heparin is attached to the free end of the PEG tethers. Alternatively, amino-dextran (70,000 MW) is used in the place of cross-linked heparin.

Dialdehydes are generated from dextran-modified surfaces by immersing the articles in an aqueous solution of freshly prepared 0.1% sodium meta-periodate for 3 hours. The periodate solution is removed and the articles immersed an aqueous solution of 1 mg/ml of poly-D-lysine (150,000–300,000 nominal MW) for 30 minutes. After rinsing in water to remove unbound poly-1-lysine, the devices are soaked in an aqueous solution of freshly prepared 0.01% sodium borohydride for 5 minutes to reduce Schiff bases. The devices are rinsed and can be stored dry. The resulting devices are characterized by having a covalently-bound hydrogel bonded to the device surfaces, such that free epsilon amines can be used for terminal modification and attachment of radioisotopes.

EXAMPLE 2

Poly-glycolide devices with a microporous structure are obtained as rods. The poly-glycolide devices are exposed to a plasma-state polymerization process with TMCTS, treated by plasma grafting of N-trimethylsilyl-allylamine, conjugated to PEG, and cross-linked heparin, or alternative amino-dextran, attached to the free end of the PEG tethers, all as described in Example 1.

EXAMPLE 3

Polyurethane urea rod devices are produced by solvent evaporation techniques to have a nominal dimension of approximately 1 mm×15 mm. The polyurethane devices are exposed to a plasma-state polymerization process with TMCTS, treated by plasma grafting of N-trimethylsilyl-allylamine, conjugated to PEG, and cross-linked heparin, or alternative amino-dextran, attached to the free end of the PEG tethers, all as described in Example 1.

EXAMPLE 4

For use with selected radioisotopes forming stable thiolate bonds, chelating groups are formed by immersing any of the devices of Examples 1, 2 or 3 in a de-gassed, aqueous solution of 100 mM sodium borate, pH 8, containing 10 mg/ml iminothiolane and 12 mM EDTA for at least 24 hours under vacuum. Alternatively N-acetylhomocysteine thiolactone may be employed. Disulfide bonds are reduced in solution containing 2 mg/ml of dithiothreitol for 15 minutes. The thiolated devices are then rinsed in a solution of 10 mM sodium-potassium tartrate, pH 3.0, containing 10 mM stannous tartrate. The devices may be dried and stored under suitable conditions.

EXAMPLE 5

To radiolabel any of the devices of Example 4 using rhenium-188, a device to be radiolabeled is immersed in a small volume of 10 mM tartrate, pH 3, containing 10 mM stannous tartrate. Re-188, in the form of Re-188-perrhenate, is obtained from a W-188/Re-188 generator and added in a small volume to the labeling vial. The labeling vial is sealed and placed in a boiling water bath for 20 minutes. After cooling, the device is rinsed to remove unbound rhenium. Ascorbic acid may be added as a stabilizing agent. The device is placed in a new vial and the radioactivity measured with a dose calibrator or beta counter prior to use in patient treatment. The radiolabeled brachytherapy device is then implanted in a patient.

EXAMPLE 6

For use with radioisotopes forming stable bonds with DTPA, DTPA is attached to the amine-modified surfaces of any of the devices of Examples 1, 2 or 3. Activated diethylenetriaminepenta-acetic acid (DTPA) is attached to the amine-modified surfaces by any of a variety of means known in the art, including use of isothiocyanates. DTPA may be conjugated to the devices by reacting an excess of 2-(p-SCN-Bz)-DTPA in the presence of the device in 0.1 M borate buffer, pH 8.5 at room temperature for a suitable period. DTPA may be used to radiolabel the device with In-111, Ga-67, Y-88, Y-90, Bi-212, and Pb-211, among other radioisotopes. The radiolabeled brachytherapy device is then implanted in a patient.

EXAMPLE 7

To radiolabel the DTPA-conjugated devices of Example 6 with Y-90, the devices are immersed in a small volume containing 10 mM phosphate, pH 7.3, and Y-90 is added. The labeling vial is placed in a boiling water bath for 20 minutes. After cooling, the device is rinsed in a solution containing 10 mM citrate, pH 6.0, to remove unbound or weakly bound Y-90. Similar methods are obtained with In-111, Ga-67, Y-88, Bi-212, and Pb-211.

EXAMPLE 8

Polycaprolactone beads are crushed into a fine powder, and the powder melted at 80° C. and cast into rods. The impregnated rods are etched with an NH3/O2 plasma to clean the rod surface, produces a micro-roughened surface, and introduces nitrogen onto the surface. TMCTS and N-trimethylsilyl-allylamine are plasma-deposited onto the surfaces using the methods as described generally in Example 1. Poly (oxyethylene)-bis-(N-hydroxybenzotriazolyl) carbonate is used to covalently attach PEG to the surface, and amino dextran (70,000 MW) is attached to the free end of the polyethylene glycol. The rods are then immersed for one hour in an aqueous solution of freshly prepared 0.1 % sodium meta-periodate containing 1 mg/ml of poly-D-lysine (150,000–300,000 nominal MW). After rinsing, the rods are soaked in an aqueous solution of freshly prepared 0.01% sodium borohydride for 5 minutes to reduce Schiff bases and rinsed.

The rods are then immersed in an aqueous solution of dextran-DTPA (500,000 MW) and an equal volume of 0.1% sodium meta-periodate is added. The freshly generated aldehydes in the dextran-DTPA crosslink to the polylysine. After rinsing, the rods are soaked in an aqueous solution of freshly prepared 0.01 % sodium borohydride for 5 minutes to reduce Schiff bases and then rinsed. The rods are dried and stored under appropriate conditions.

To radiolabel, the rods are immersed for 15 minutes in an aqueous solution of Y-90. The Y-90 is chelated by DTPA attached to the rod and the unbound Y-90 rinsed off. The radiolabeled brachytherapy device is then implanted in a patient.

EXAMPLE 9

Polycaprolactone beads are crushed into a fine powder and mixed with powdered paclitaxel, a chemotherapy agent. The mixed powder is melted at 80° C. and cast into rods. The drug-impregnated rods are etched with an NH3/O2 plasma to clean the rod surface, produces a micro-roughened surface, and introduces nitrogen onto the surface. TMCTS and N-trimethylsilyl-allylamine are plasma-deposited onto the surfaces using the methods as described generally in Example 1. Poly (oxyethylene)-bis-(N-hydroxybenzotriazolyl) carbonate is used to covalently attach PEG to the surface, and amino dextran (70,000 MW) is attached to the free end of the polyethylene glycol. The rods are then immersed for one hour in an aqueous solution of freshly prepared 0.1% sodium meta-periodate containing 1 mg/ml of poly-D-lysine (150,000–300,000 nominal MW). After rinsing, the rods are soaked in an aqueous solution of freshly prepared 0.01% sodium borohydride for 5 minutes to reduce Schiff bases and rinsed.

The rods are then immersed in an aqueous solution of dextran-DTPA (500,000 MW) and an equal volume of 0.1% sodium meta-periodate is added. The freshly generated aldehydes in the dextran-DTPA crosslink to the polylysine. After rinsing, the rods are soaked in an aqueous solution of freshly prepared 0.01% sodium borohydride for 5 minutes to reduce Schiff bases and then rinsed. The rods are dried and stored under appropriate conditions.

To radiolabel, the rods are immersed for 15 minutes in an aqueous solution of Y-90. The Y-90 is chelated by DTPA attached to the rod and the unbound Y-90 rinsed off. The radiolabeled combination chemotherapy and brachytherapy device is then implanted in a patient.

EXAMPLE 10

Gelfoam pad or rod devices, fabricated from gelatin, are obtained and immersed in an aqueous solution of dextran-DTPA (500,000 MW) containing an equal volume of 0.1% sodium meta-periodate. The freshly generated aldehydes in the dextran-DTPA crosslink to the epsilon amine of lysine groups in the devices. After rinsing, the pads are soaked in an aqueous solution of freshly prepared 0.01% sodium borohydride for 5 minutes to reduce Schiff bases and then rinsed. The pads are then optionally lyophilized under nitrogen for convenient storage.

To radiolabel, the pads are immersed for 15 minutes in an aqueous solution of Y-90. Y-90 is chelated by the DTPA and unbound or weakly bound Y-90 is removed by rinsing. The radiolabeled device is dipped in a chloroform solution containing 5% polycaprolactone and paclitaxel. The device is air dried and the combination chemotherapy and brachytherapy device is implanted in a patient.

EXAMPLE 11

Brachytherapy devices are made from any available source of collagen, such as gelfoam materials prepared from gelatin. The brachytherapy devices are optionally made with an imbedded chemotherapy drugs, such as paclitaxel. The devices are acidified and stored dry until to use. To radiolabel, microaggregated albumin is radiolabeled with Re-188 and then mixed immediately before use with the acidified collagen device that optionally contains a chemotherapeutic drug. The combination chemotherapy and brachytherapy device is implanted in a patient and undergoes gelation as the pH transits to neutral.

EXAMPLE 12

Poly-lactide or poly-glycolide rods with a microporous structure are obtained and dipped in a saturated ethanolic solution of paclitaxel and allowed to air dry. The rods are then subjected to repeated cycles of dipping and air drying resulting in layers of paclitaxel being deposited in and on the porous matrix. After the last cycle of air-drying, the paclitaxel-impregnated rods are coated by dipping into an 1:1 solution of 5% poly hydroxyethyethyl methacrylate. Subsequently TMCTS and N-trimethylsilyl-allylamine are plasma-deposited onto the rod as generally described in Example 1. Poly (oxyethylene)-bis-(N-hydroxybenzotriazolyl) carbonate is used to covalently attach PEG to the surface, and amino dextran (70,000 MW) is attached to the free end of the polyethylene glycol. The rods are then immersed for one hour in an aqueous solution of freshly prepared 0.1% sodium meta-periodate containing 1 mg/ml of poly-D-lysine (150,000–300,000 nominal MW). After rinsing, the rods are soaked in an aqueous solution of freshly prepared 0.01% sodium borohydride for 5 minutes to reduce Schiff bases and rinsed.

The rods are then immersed in an aqueous solution of dextran-DTPA (500,000 MW) and an equal volume of 0.1% sodium meta-periodate is added. The freshly generated aldehydes in the dextran-DTPA crosslink to the polylysine. After rinsing, the rods are soaked in an aqueous solution of freshly prepared 0.01% sodium borohydride for 5 minutes to reduce Schiff bases and then rinsed. The rods are dried and stored under appropriate conditions.

To radiolabel, the rods are immersed for 15 minutes in an aqueous solution of Y-90. The Y-90 is chelated by DTPA attached to the rod and the unbound Y-90 rinsed off. The radiolabeled combination chemotherapy and brachytherapy device is then implanted in a patient.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A radiation delivery device, said device comprising:
    a bioabsorbable structure having a predefined persistence period when implanted in a patient wherein the bioabsorbable structure is formed as an implantable macrostructure comprising a continuous core structure with a minimum width of at least 1 mm; and
    a radionuclide having a known half-life immobilized on said structure, where the persistence period of the bioabsorbable structure is substantially longer than a half-life of the radionuclide so that loss of radioactivity from the target site is minimized.

2. A radiation delivery device as in claim 1, wherein the bioabsorbable structure has a persistence period in the range from 2 days to 90 days.

3. A radiation delivery device as in claim 1 or 2, wherein the radionuclide has a half-life of 60 days or less.

4. A radiation device as in claims 1 or 2, wherein the bioabsorbable structure is composed of a biological polymer.

5. A radiation device as in claims 1 or 2, wherein the bioabsorbable structure has a drug incorporated into said structure.

6. A radiation device as in claim 5, wherein the drug incorporated into the biodegradable structure is substantially released within two half-lives of the radionuclide.

7. A radiation device as in claim 5, wherein the drug incorporated into the biodegradable structure is a chemotherapeutic agent.

8. A radiation delivery device as in claim 1, wherein the radionuclide is selected from the group consisting of Cu-162, Cu-64, Cu-67, Ru-97, Rh-105, Pd-109, Sm-153, Ho-166, Re-186, Re-188, Au-198, Au-199, Pb-203, Pb-211, Bi-212, I-125, I-131, Y-90, Pd-103, Ir-192 and P-32.

9. A radiation delivery device as in claim 1, wherein the radionuclide is covalently bound to a preformed surface on the bioabsorbable structure.

10. A radiation delivery device as in claim 9, wherein the radionuclide is covalently bound through a linker which is bound to the surface.

11. A radiation delivery device as in claim 1, wherein the radionuclide is chelated, adsorbed, precipitated, or complexed to a preformed surface on the bioabsorbable structure.

12. A method for localized delivery of radioactivity to a target site in tissue, said method comprising implanting a radiation delivery device, wherein said device comprises:
    a radiation delivery device said device comprising:
    a bioabsorbable structure having a predefined persistence period when implanted in a patient;
    wherein the bioabsorbable structure is formed as an implantable macrostructure comprising a continuous core structure with a minimum width of at least 1 mm; and
    a radionuclide having a known half-life immobilized on said structure where the persistence period of the bioabsorbable structure is substantially longer than a half-life of the radionuclide so that loss of radioactivity from the target site is minimized.

13. A method for localized delivery of radioactivity and drugs to a target site in tissue, said method comprising implanting a radiation delivery device at said target site, wherein said device comprises:
    a bioabsorbable structure having a predefined persistence period when implanted in a patient;
    a radionuclide having a know half-life immobilized on said structure where the persistence period of the bioabsorbable structure is substantially longer than a half-life of the radionuclide so that loss of radioactivity from the target site is minimized; and
    a drug incorporated into said structure.

14. A method as in claim 12 or 13, wherein implanting comprises surgically exposing the target site and placing the device at the surgically exposed site.

15. A method for preparing a treatment delivery device, said method comprising:
    providing a bioabsorbable structure having a predefined persistence period and a surface wherein at least a portion of the surface has been coated with a substrate material;
    providing a radioactive material including a bonding constituent which is capable of bonding to the substrate material and a radioactive isotope, where the persistence period of the bioabsorbable structure is substantially longer than a half-life of the radionuclide;
    determining the specific activity of the radioactive material; and
    bonding an amount of the radioactive material to the substrate material on the structure selected to provide a predetermined radioactive dosage.

16. A method as in claim 15, wherein the predetermined dosage is in the range from 20 gray to 200 gray.

17. A method as in claim 15, wherein the bioabsorbable structure has a persistence period in the range from 2 days to 90 days.

18. A method as in claim 15 or 17, wherein the radionuclide has a half-life of 60 days or less.

19. A method as in claim 15, wherein the bonding step comprises covalently bonding the radioactive material to the substrate material.

20. A method as in claim 15, wherein the biodegradable structure is composed of a biological polymer.

21. A method as in claim 15 or 20, wherein the biodegradable structure is formed as an implantable macrostructure comprising a continuous core structure with a minimum width of at least 1 mm.

22. A method as in claim 15 or 20, wherein the biodegradable structure is formed as an implantable microstructure comprising core particles having an average width below 1 mm.

23. A method as in claim 15, wherein the substrate material is selected from the group consisting of siloxanes and bifunctional chelating agents.

24. A method as in claim 15, wherein the radioactive material comprises a radionuclide and a bonding component.

25. A method as in claim 15, wherein the bioabsorbable structure has dispersed therein a drug.

26. A method as in claim 15, further comprising the steps of:
    providing a sustained release drug material which is capable of bonding to the substrate material, where the persistence period of the bioabsorbable structure is substantially longer than the period required to release substantially release the drug; and bonding an effective amount of the sustained release drug material to the substrate material on the device.

27. A method as in claims 25 or 26, wherein the drug is a chemotherapeutic drug.

28. A kit comprising:

a radiation delivery device, said device comprising:

a bioabsorbable structure having a predefined persistence period when implanted in a patient;

wherein the bioabsorbable structure is formed as an implantable macrostructure comprising a continuous core structure with a minimum width of at least 1 mm;

a radionuclide having a known half-life immobilized on said structure, where the persistence period of the bioabsorbable structure is substantially longer than a half-life of the radionuclide so that loss of radioactivity from the target site is minimized; and instructions describing a method for implanting the device in tissue.

29. A kit as in claim 28, further comprising a package which contains the device and the instructions.

30. A kit as in claim 29, wherein the instructions further set forth a method for coating the radiation delivery device with a radioactive material prior to implantation.

* * * * *